United States Patent
Fuchs et al.

(10) Patent No.: US 11,395,876 B2
(45) Date of Patent: Jul. 26, 2022

(54) STERILE PUMP MODULE FOR AN INFUSION PUMP

(71) Applicant: B. BRAUN MELSUNGEN AG, Melsungen (DE)

(72) Inventors: Jürgen Fuchs, Bad Emstal (DE); Jürgen Hartung, Helsa (DE); Jürgen Steger, Körle (DE)

(73) Assignee: B. BRAUN MELSUNGEN AG, Melsungen (DE)

( * ) Notice: Subject to any disclaimer, the term of this patent is extended or adjusted under 35 U.S.C. 154(b) by 163 days.

(21) Appl. No.: 16/616,018

(22) PCT Filed: May 23, 2018

(86) PCT No.: PCT/EP2018/063509
§ 371 (c)(1),
(2) Date: Nov. 22, 2019

(87) PCT Pub. No.: WO2018/215542
PCT Pub. Date: Nov. 26, 2018

(65) Prior Publication Data
US 2020/0086041 A1    Mar. 19, 2020

(30) Foreign Application Priority Data
May 23, 2017   (DE) .................... 10 2017 111 299.5

(51) Int. Cl.
*A61M 5/142*      (2006.01)
*A61M 5/315*      (2006.01)
(Continued)

(52) U.S. Cl.
CPC .... *A61M 5/14216* (2013.01); *A61M 5/31513* (2013.01); *A61M 39/287* (2013.01); *A61M 39/24* (2013.01)

(58) Field of Classification Search
CPC .......... A61M 5/14216; A61M 5/31513; A61M 5/1456; A61M 39/287; A61M 5/1413; A61M 39/24
See application file for complete search history.

(56) References Cited

U.S. PATENT DOCUMENTS 3,901,231 A    8/1975   Olson
3,985,133 A    10/1976  Jenkins et al.
(Continued)

FOREIGN PATENT DOCUMENTS

CN    1433816 A      8/2003
CN    104204517 A    12/2014
(Continued)

OTHER PUBLICATIONS

Office Action received in Chinese Application No. 20188044269.6 dated May 19, 2021, with translation, 11 pages.
(Continued)

*Primary Examiner* — James D Ponton
*Assistant Examiner* — Neeraja Gollamudi
(74) *Attorney, Agent, or Firm* — Christopher A. Rothe; Culhane Meadows, PLLC

(57) ABSTRACT

A pump module for an infusion pump includes a plunger-cylinder unit that can be coupled to the infusion pump in order to deliver fluid from a fluid feed line into a fluid drain line to a patient. The plunger-cylinder unit has a delivery chamber that is fluidically connected to the fluid feed line and the fluid drain line. The delivery chamber is delimited by the cylinder (14). The plunger can be moved linearly/back and forth in the axial direction. A plunger seal seals the plunger in relation to the cylinder. The section of the wall of the cylinder, over which the plunger seal passes during the back-and-forth motion of the plunger, is sealed in a sterile manner in relation to the surroundings.

18 Claims, 8 Drawing Sheets

(51) Int. Cl.
*A61M 39/24* (2006.01)
*A61M 39/28* (2006.01)

(56) References Cited

U.S. PATENT DOCUMENTS

| | | | |
|---|---|---|---|
| 4,515,591 A * | 5/1985 | Hemmrich et al. | ............................ A61M 5/14216 604/152 |
| 4,689,043 A | 8/1987 | Bisha | |
| 7,422,570 B2 | 9/2008 | Gerlach et al. | |
| 9,427,517 B2 | 8/2016 | Eberhard | |
| 9,511,186 B1 * | 12/2016 | Nystrom | ............ A61M 5/1456 |
| 9,586,008 B2 | 3/2017 | Shetty et al. | |
| 2002/0165503 A1 * | 11/2002 | Morris et al. | ....... A61M 39/287 604/250 |
| 2005/0119620 A1 | 6/2005 | Tachikawa et al. | |
| 2010/0152674 A1 | 6/2010 | Kavazov et al. | |
| 2011/0150680 A1 | 6/2011 | Dion et al. | |
| 2012/0215200 A1 | 8/2012 | Matsuura et al. | |
| 2014/0194778 A1 | 7/2014 | Uziel et al. | |
| 2014/0303560 A1 | 10/2014 | Yates et al. | |
| 2014/0314594 A1 | 10/2014 | Jones et al. | |

FOREIGN PATENT DOCUMENTS

| | | |
|---|---|---|
| CN | 105530977 A | 4/2016 |
| DE | 102014224819 A1 | 6/2016 |
| EP | 0110276 A2 * | 6/1984 ........ A61M 5/14216 |
| EP | 2902052 A1 | 8/2015 |
| GB | 2126666 A | 3/1984 |
| JP | 2003199827 A | 7/2003 |
| JP | 2004534598 A | 11/2004 |
| JP | 2006271665 A | 10/2006 |
| KR | 100985446 B1 | 10/2010 |
| RU | 2019191 C1 | 9/1994 |
| WO | 9924098 A1 | 5/1999 |
| WO | 03006099 A1 | 1/2003 |
| WO | 2010048414 A2 | 4/2010 |

OTHER PUBLICATIONS

German Search Report for German Application No. 10 2017 111 299.5, with English translation, dated Nov. 29, 2017, 12 pages.
International Search Report and Written Opinion for International Application PCT/EP2018/063509, dated Sep. 10, 2018, 7 pages.
International Search Report and Written Opinion for International Application PCT/EP2018/063510, dated Sep. 10, 2018, 8 pages.
International Search Report and Written Opinion for International Application PCT/EP2018/063511, dated Sep. 10, 2018, 8 pages.
Office Action received in Japanese Application No. 2019-564846 dated Jan. 4, 2022, with translation, 5 pages.
Office Action received in Russian Application No. 2019142689/14 dated Sep. 10, 2021, with translation, 14 pages.
Search Report received in Russian Application No. 2019142689/14 dated Sep. 9, 2021, with translation, 5 pages.

* cited by examiner

STERILE PUMP MODULE FOR AN INFUSION PUMP

CROSS-REFERENCE TO RELATED APPLICATIONS

This application is the United States national phase entry of International Application No. PCT/EP2018/063509, filed May 23, 2018, which claims the benefit of priority of German Application No. 10 2017 111 299.5, filed May 23, 2017. The contents of International Application No. PCT/EP2018/063509 and German Application No. 10 2017 111 299.5 are incorporated by reference herein.

FIELD

The present invention relates to a pump module for an infusion pump comprising a separate piston-cylinder unit adapted for selective/changeable coupling with the infusion pump (1) for delivering fluid from a fluid feed line to a fluid drain line to a patient, wherein the piston-cylinder unit comprises a delivery chamber fluidically connected to the fluid feed line and the fluid drain line, and which is delimited by the cylinder, the piston which is arranged therein so as to be movable translationally/forwards and backwards in the axial direction, and a piston seal sealing the piston with respect to the cylinder. It further relates to an infusion pump for delivering fluid from a fluid source to a patient comprising such a pump module.

BACKGROUND

In infusion technology, flexible tube pumps as well as syringe pumps are commonly known in order to deliver fluid to a patient. For applications that place high demands on dosing accuracy, syringe pumps are generally used, as they easily achieve a defined fluid delivery. For applications that require a higher delivery volume of fluid, flexible tube pumps are well suited, as they deliver largely continuously and without discrete delivery volume due to their conveying technology.

Such applications of an infusion pump are known from the prior art, in which relatively high delivery volumes have to be paired with high delivery accuracy, which leads to significant problems. Syringe pumps have the disadvantage that the fluid volume that can be conveyed with them is limited by the volume of the syringe used. Flexible tube pumps, on the other hand, can achieve relatively large delivery volumes, but have the disadvantage of low delivery accuracy. Particularly with small feed rates, their delivery accuracy is not guaranteed due to the peristalsis commonly used. In addition, the drive of a flexible tube pump is usually relatively large and heavy and consumes a comparatively large amount of power due to the flexing of the pump hose by the peristaltic drive.

An infusion pump of the Applicant specially developed for such applications with relatively high delivery volume as well as high delivery accuracy works with a pump module with a piston-cylinder unit as pump unit. It is configured to be actuated by a drive mechanism of the infusion pump consisting of an electric drive motor as well as a transmission gearing to transform the rotational movement of the drive motor into a translational/back/forth movement of the piston mounted displaceably in the cylinder. The drive mechanism is preferably controlled by a control/regulation unit of the infusion pump. The pump module also includes a valve device, which is preferably connected to the control/regulation unit and which is adapted, if necessary, in a regulated/controlled manner in the case of a pump delivery stroke, to interrupt a connection between the piston-cylinder unit as fluid intermediate storage and a delivery terminal to a separate fluid large volume as well as to open a connection between the piston-cylinder unit and a patient port and, in the case of a pump suction stroke, to open the connection between the piston-cylinder unit and the delivery terminal to the separate fluid large volume as well as to block the connection between the piston-cylinder unit and the patient port.

From U.S. Pat. No. 3,901,231 A, an infusion pump for delivering intravenous fluid from a conventional syringe to a patient is known. The pump is adaptable to adjust the amplitude of the syringe stroke to determine the amount of fluid delivered to the patient over a period of time.

From U.S. Pat. No. 3,985,133 a pump module with a piston-cylinder unit is known, whose piston can be coupled with a pump drive to inject fluid from a fluid reservoir into the bloodstream of a patient. A similar pump module is known from U.S. Pat. No. 4,396,385 A, wherein the cylinder chamber is closed with a cover arranged on the one hand on the cylinder and on the other hand on the piston. The disadvantage of this pump module is that the cover protrudes unprotected from the cylinder and can possibly be easily damaged so that contaminations can penetrate into the cylinder chamber. A further disadvantage is that the rotary valves used are relatively complex in terms of their actuation and are not very reliable.

It is particularly important that the pump module is and remains absolutely sterile in its areas of contact with the liquid to be administered, in particular infusion fluid or a medication. Established piston pumps of this type have the disadvantage that their oscillating piston can be contaminated by the surrounding air, for example, and germs can penetrate into the liquid to be conveyed and may be administered to the patient.

SUMMARY

Based on the above problem, the invention is based on the object of eliminating the previously mentioned disadvantages, in particular to provide a pump module as well as a medical infusion pump that can replace known systems, is universally applicable particularly in applications with high volume delivery and high delivery accuracy, and is absolutely sterile and remains sterile during use in areas that come into contact with a fluid to be administered to a patient. In particular, sterility is to be guaranteed. In addition, the pump module is to be mountable in the pump in a particularly user-friendly manner, wherein the sterility of the pump module is not endangered during handling, use, or storing of the pump module. Preferably, the size is to be small compared to known systems. Furthermore, it is to be simple and inexpensive and preferably operable by means of a rechargeable battery.

This object is solved according to the invention by a pump module, in particular an infusion/syringe pump module, for a medical infusion pump to convey fluid from a fluid source to a patient as well as by an infusion pump.

The object is solved in particular by a pump module for an infusion pump, which has a piston-cylinder unit which can be coupled to the infusion pump, in particular a separate piston-cylinder unit adapted for selective/changeable coupling with the infusion pump (1) for delivering fluid from a fluid feed line into a fluid drain line to a patient, wherein the piston-cylinder unit comprises a delivery chamber fluidically connected to the fluid feed line and the fluid drain line and which is delimited by the cylinder, the piston is arranged therein so as to be movable translationally/forwards and backwards in the axial direction, in particular in the axial direction of the piston-cylinder unit, and a piston seal sealing the piston with respect to the cylinder, wherein the wall portion of the cylinder passed by the piston seal during the forward/backward movement of the piston is sealed against the environment in a sterile manner, in particular wherein the piston seal has a sleeve portion extending along the piston and surrounding it in a relatively movable manner, which is configured to be movable relative to the piston and is held loosely between a circumferential portion/wall portion of the cylinder and the piston and is sealingly fixed to the cylinder at an end or end region of the cylinder facing away from the delivery chamber, such that the circumferential portion/wall portion of the cylinder passed by the piston seal during the forward/backward movement of the piston is sealed against the environment in a sterile manner. The object is also solved by an infusion pump with a pump module according to the invention, in particular according to the present description. The advantage and effect of this invention over the prior art is that the oscillating pump element, here in the form of the piston-cylinder unit, is protected against germs by the sealing element, in particular in the areas that come into contact with the fluid to be administered to a patient. These areas are in particular the sections of the cylinder wall that are swept by the piston seal during the piston stroke. The piston-cylinder unit is preferably a smooth-running unit in order to keep actuating forces low and to achieve a high delivery accuracy.

Advantageous embodiments of the invention are explained in more detail below.

According to an embodiment of the invention, the piston displacement, which is located on the side of the piston seal opposite the delivery chamber, in particular the entire piston displacement, can be sealed in a sterile manner against the environment by means of an elastic sealing element arranged inside the piston displacement. In particular, the sealing element can in particular be a membrane that seals the proximal piston displacement in a sterile manner from the environment; as a result of its elasticity, it can compensate for the relative positional changes between the piston and the cylinder caused by moving the piston forwards and backwards. It may also be located on the proximal end of the piston, on the one hand, and on the proximal end of the cylinder, on the other hand, and/or be firmly connected to it. Proximal in this context means on the sides of the pump, distal on the sides of the delivery chamber. In a preferred embodiment, the sealing element is configured and arranged on the cylinder and on the piston in such a way that it does not protrude beyond the proximal end of the cylinder, in particular regardless of the respective position of the piston in the cylinder. In this way, the sealing element is arranged inside the cylinder in a protected manner so that accidental damage during storing, assembly and/or use of the pump module can be safely prevented. This helps to ensure the sterility of the areas of the pump module that come into contact with a fluid to be administered to a patient.

Within the scope of the invention, the sealing element may also have a wall portion formed as bellows and extending in particular in the axial direction. It can preferably be arranged inside the cylinder so that it is protected against damage. Such a bellows takes up little space and is also subject to relatively low loads during operation of the pump module due to the deformation imposed on it, so that the pump module can be formed small and robust.

A particularly robust embodiment of the invention provides that the sealing element on its side facing away from the piston has an in particular annular coupling portion for sealing arrangement at and/or sealing connection to the cylinder. This can be connected to the cylinder by means of a border, in particular it can be tightly connected. The border can, for example, be formed by flanging a proximal end section of the cylinder, in particular the cylinder wall. Alternatively or additionally, the sealing element can be connected in a sealing manner to the piston with its side facing the piston. In particular, it can be connected to the front side of the piston. For example, the sealing element is connected to the piston by a material connection. In particular, it can be designed in one piece with the piston, e.g. by manufacturing the piston and the sealing element using two-component injection molding. The coupling portion can in particular be formed as a sealing plate.

According to a particularly user-friendly embodiment, the piston can have a coupling structure for detachable coupling with a corresponding coupling element of the drive mechanism of the infusion pump. Especially advantageously, the coupling structure can be formed radially inside the sealing element, in particular radially inside the wall portion of the sealing element formed as a bellows. For example, the coupling structure may have a blind hole, in particular a central blind hole, inserted into the proximal front surface of the piston in the axial direction. This allows a particularly short construction length of the piston and thus of the pump module. In order to enable a particularly simple coupling of pump module and infusion pump, the coupling structure can have an internal latching structure for the latching insertion of a piston rod of the drive mechanism. The piston is or can be arranged by means of the coupling structure in particular on a piston rod of the infusion pump. The coupling element can, for example, be formed as a plug-in coupling and can be automatically or inevitably coupled to the drive when the pump module is arranged as intended in the infusion pump. The coupling preferably has latching structures which hold the two coupling elements together and, in particular, allow the two coupling elements to engage audibly and/or perceptibly for an operator.

One embodiment of the invention is characterized in that the piston-cylinder unit comprises a proximal piston seal and a distal piston seal. These seal both between the piston and the cylinder and ensure the sterility of the delivery chamber. It is particularly within the scope of the invention that the pump module has only proximal and distal piston seals and no sealing element connected to the piston and the cylinder. Preferably, the proximal piston seal and the distal piston seal are arranged plane-parallel to each other. Alternatively or additionally, the distance in the direction of the longitudinal axis between the proximal piston seal and the distal piston seal is greater than the delivery stroke of the piston-cylinder unit/of the piston in the cylinder. Preferably, the distance between the two piston seals is at least 1 mm to 3 mm, in particular 2 mm greater than the stroke of the piston pump (and thus than the stroke of the piston in the cylinder). This ensures that the area coming into contact with the fluid to be administered is always absolutely sterile. The proximal piston seal and/or the distal piston seal can be formed in one piece with the piston, e.g. by being molded onto the piston using two-component injection molding. The piston seal(s) can basically be designed in the form of a flexible sealing lip or sealing lips within the scope of the invention. A particular advantage of the embodiment described above with a proximal and a distal piston seal is that the piston-cylinder unit is particularly smooth-running and actuating forces are low, so that high delivery accuracy and efficiency can be achieved. It can also be said that the piston and the distance between the two piston seals in the axial direction are longer than the maximum filling level of the cylinder, which prevents ambient air, which is naturally outside the cylinder, from mixing with the medium inside the cylinder or from contaminating areas of the piston-cylinder unit that come into contact with the fluid to be delivered. The combination of two piston seals/sealing lips and piston/cylinder length results in an effective barrier against entering germs. A further advantage is that this embodiment with two piston seals can withstand relatively high pressure differences during fluid delivery without the fluid and/or air to be pumped being able to overcome the seal/sealing lip between piston and cylinder. It can therefore also be said that the piston has one seal/sealing lip for sealing against overpressure and one seal/sealing lip for sealing against low pressure. Thus, a low-pressure movement and a high-pressure movement of the piston are sealed to ensure the sterility of a fluid space/dosing space, i.e. the space in which the fluid to be conveyed is located in the cylinder. In this way, the pump meets the high requirements for cleanliness in a medical environment. The piston preferably has an essentially round cross-section, resulting in approximately ring-shaped piston seals.

In a particularly storing friendly embodiment of the invention, which allows a relatively long storage of the pump module without significant impairment of the sealing effect the piston seal(s), the cylinder is provided with a number of annular grooves corresponding to the number of piston seals, i.e. in the case of only one piston seal on its inner surface facing the piston with only one circumferential annular groove, to receive the piston seal in a storing position/rest position therein. In the case of a piston with a proximal and a distal piston seal, the cylinder is provided on its inner surface facing the piston with a proximal circumferential annular groove and a distal circumferential annular groove, whose distance from each other in the longitudinal direction is equal to the distance of the proximal piston seal and the distal piston seal in the longitudinal direction. The annular groove(s) is/are preferably arranged so that they are outside the working range of the piston.

One embodiment of the invention is characterized in that the cylinder has at its distal end a cylinder head in which at least one fluid passage is formed to fluidly connect the delivery chamber to the fluid feed line and/or to the fluid drain line. The cylinder head can in particular distally delimit the delivery chamber. A particularly user-friendly embodiment of the invention, which can be easily coupled with the infusion pump, provides that a handle portion or handle piece is arranged distally on the cylinder, in particular on its cylinder head, for handling of the pump module when coupling and uncoupling with the infusion pump.

According to an embodiment of the invention, the piston-cylinder unit can be provided with a first tube portion as inlet feed line/fluid feed line and a second tube portion as patient-side outlet feed line/fluid drain line. At least one or both tube portions can be firmly connected to the piston-cylinder unit, in particular to the cylinder head, e.g. in one piece, friction-locked or material-locked, e.g. by injection in the case of plastic parts.

The fluid feed line or respectively the first tube portion can be provided with a Luer-Lock coupling piece at the end opposite the piston-cylinder unit. This can be formed in particular as a Luer-Lock internal cone. Alternatively or additionally, the fluid drain line or respectively the second tube portion can be provided with a Luer-Lock coupling piece at the end opposite the piston-cylinder unit. This can in particular be formed as a Luer-Lock outside cone. This allows a connection of the pump module or respectively the fluid conduit system contained in it with an extracorporeal line or conduit system that is particularly easy to operate. The invention can therefore be used easily and in a well-known way together with existing and widely used medical technology equipment. As an alternative to a Luer-Lock connection, a drip chamber connected to the patient can be provided or the second tube portion is designed as a bag line with a closed end and can be connected with an insertion spike. In addition or alternatively, the arrangement of a spike/injection spike is also possible to increase the flexibility in the area of application or the compactness of the pump.

According to one embodiment, the pump module can have a sliding clamp which is adjustable, i.e. displaceable, in such a way that it selectively releases or blocks a fluid flow from or to the piston-cylinder unit, in particular in the first and/or second tube portion. The sliding clamp can be adjusted in such a way that no air bubbles form after starting up the pump module. The sliding clamp can preferably be clipped onto the handle portion or the handle piece of the pump module so that it can easily be made of a different material than the rest of the pump module.

An advantageous embodiment of the invention is distinguished in that a sleeve/ring is arranged at one end of the pump module or the handle portion/piece facing away from the sliding clamp. This sleeve is able to fix the fluid feed line and/or the fluid drain line and/or the first and/or the second tube portion and thus allows safe coupling of an infusion line with the pump module. It therefore serves as a holding ring through which the infusion line can be threaded.

The piston-cylinder unit can in particular be adapted to be actuated by means of a drive mechanism, in particular by means of a drive mechanism of the infusion pump according to the invention, for example consisting of an electric drive motor as well as a transmission gearing for transforming the rotational movement of the drive motor into a translational movement/forward/backward movement of the piston mounted displaceably in the cylinder. The drive mechanism can also be controlled by a control/regulation unit of the infusion pump. In addition, a valve device may be provided, for example the infusion pump may have a valve device connected to the control/regulation unit and be configured to interrupt (optionally in a regulated/controlled manner) in case of a pump delivery stroke, a connection between the piston-cylinder unit as fluid intermediate storage and a delivery terminal to a separate fluid large volume as well as to release a connection between the piston-cylinder unit and a patient port and, in case of a pump suction stroke, to open the connection between the piston-cylinder unit and the delivery terminal to the separate fluid large volume as well as to block the connection between the piston-cylinder unit and the patient port.

In the simplest case, the valve device has passively-operable valve elements, i.e. the valve device preferably has two check valves, which are housed in (separate, as disposable items designed) connection lines to the patient port and to the fluid large volume, which can be inserted into the infusion pump. This has the advantage that the valve device can be manufactured at a particularly low price and can therefore be disposed of as a disposable item together with the entire fluid conduit system.

Alternatively, it may be provided to equip the valve device with actively-actuable valve elements, preferably two tube pinchers/compressors, which can act on flexibly deformable sections of the two connection lines for their sealing compression and which are preferably housed in the infusion pump (or pump module). In concrete terms, therefore, the fluid conduit system, which is preferably designed as a disposable article, has a first, preferably elastically deformable tube portion for supplying fluid (from the large fluid reservoir into the intermediate reservoir) and a second, preferably elastically deformable tube portion for discharging fluid (from the intermediate reservoir in the direction towards the patient), wherein the two tube portions have intermediate liquid reservoirs for insertion into the infusion pump as well as for connection to the piston-cylinder unit for sucking fluid from the first tube portion into the intermediate liquid reservoir. The tube pinchers/compressors can preferably be configured as punches/tappers or as scissor clamps or similar mechanical clamping devices which are movably mounted in the infusion pump (thus being part of the infusion pump) and can each be operated by a drive which is connected to the control/regulation unit. This variant enables controlled and thus safe opening and closing of the respective liquid/fluid lines and also a fluid conduit system that can be manufactured at a lower price. The characteristic feature here is that the two tube pinchers/compressors located in the inlet and outlet are mechanically coupled to each other in such a way that at least one side securely squeezes the hose. The tube pinchers/compressors are preloaded with springs, for example, so that they bridge the otherwise leaking positions so that no leaking position occurs when changing between inlet and outlet. Alternatively, the control time of the valves can also be set via e.g. cam disks or by separate drives using motors.

Via the control unit, which can be implemented, for example, in the form of a motor-driven valve control system, the hose in the outlet, i.e. the second tube portion, can be blocked, preferably squeezed off, when the piston-cylinder unit/syringe is retracted. Moreover, the hose in the inlet, i.e. the first tube portion, can be blocked, preferably squeezed off, when the piston-cylinder unit/syringe is pushed out. It is characteristic that the piston-cylinder unit/syringe can be driven like a piston pump. Altogether, the invention makes it possible to convey large fluid quantities/volumes in infusion applications in the broadest sense with the high precision of a piston pump/syringe pump. The high precision is due to the fact that the delivery rate/flow amount is very precise, since the delivery is carried out with the piston-cylinder unit. Changes in the delivery volume, i.e. the volume of the cylinder chamber, can be precisely adjusted and controlled over a wide feed rate range. Leakage flows can be essentially completely prevented by this design. The disadvantage of the limited flow rate usually present with piston pumps is eliminated in the sense of the invention in that the piston-cylinder unit is continuously filled and emptied alternately, which is made possible by the control according to the invention of the inflows and outflows to and from the piston-cylinder unit. One way to achieve a largely constant feed rate is to combine two pumps according to the invention or to provide the pump with two piston-cylinder units and their associated control units, which are operated with phase shifts.

A preferred embodiment of the infusion pump according to the invention is characterized in that the control unit and the drive are arranged at/in a housing part of the infusion pump. The pump module can in particular be arranged on the housing part so that it can be exchanged by the user. It should preferably be placed inside and/or be removed from the pump without the use of special tools or devices. The pump module according to the invention can in particular be designed as a single-use article and be intended for single use in the pump. This is particularly advantageous and user-friendly with regard to sterile conditions. It can, for example, be implemented in the form of a disposable syringe, with the delivery volume opening of which the two tube portions are fluidically connected. This can be realized in such a way that the two tube portions form a continuous fluid line which is provided with a branch in an area between the deformation points for connecting the piston-cylinder unit, in particular a disposable syringe. Alternatively, the piston-cylinder unit/the disposable syringe can have two flow openings, an outlet and an inlet, each of which is fluidically connected to the corresponding tube portion.

It is of particular advantage if the drive of the piston-cylinder unit is a linear drive/motor located in the axis of motion of the piston. It is particularly preferred if the drive is arranged and designed in such a way that forces acting on the piston from the drive are applied centrally and in the axial direction. A particular advantage is that forces acting on the piston can be minimized (in comparison to decentralized force introduction) and thus only a small amount of energy is required to actuate the piston-cylinder unit. As a result, the drive and thus the pump can be small, which leads to savings in terms of weight, costs and installation space. Furthermore, high precision can be achieved by the central application of operating forces in the piston. Using a small syringe as a piston-cylinder unit allows a linear drive to be arranged directly in the axis of the syringe piston, thus ensuring that no transverse forces affecting the accuracy act on the syringe piston. Furthermore, a small cross section of the syringe produces only small forces, allowing the use of a simple, cost-efficient drive, such as a linear stepper motor. The construction size of the pump can therefore be significantly smaller than with known infusion pumps.

The pump according to the invention can also have a second drive, in particular a linear drive/motor, for the control unit. The two drives for the piston-cylinder unit and the control unit can be coupled together for control purposes in such a way that the control function described above is performed by squeezing the two tube portions shut.

According to a further embodiment, the pump may have a receptacle for the pump module. This can, for example, be in the form of a recess in a pump housing and, in particular, can be closed by means of a closure (for example, in the form of a cover flap arranged pivotably on the pump, in particular on its housing). In particular, the closure can be locked with the housing part via a locking unit in a position closing the receptacle. The closure, the receptacle and the pump module can be matched to each other in such a way that closing (and if necessary locking) of the closure is only possible if the pump module is arranged and connected as intended and in the correct manner. In this way, a user can be given feedback with regard to error-free installation and use of the pump, which increases patient safety in an advantageous way. Furthermore, by closing the cover flap, an automatic coupling of the piston-cylinder unit with the drive can be achieved, which is a particularly simple and safe operation. A housing of the pump can in particular consist of a lower housing part, on which the entire mechanics and electronics can be arranged and held, as well as an upper housing part, which can in particular have a display and various switching elements. Inside the housing there can be a locking mechanism for the cover flap.

One embodiment of the infusion pump is characterized by the fact that the control unit has a motor-driven tilting-lever unit. This can be designed and operated in such a way that in a first tilting position it squeezes the first tube portion and opens the second tube portion and in a second tilting position, it squeezes the second tube portion and opens the first tube portion.

In particular, the control unit may have a pressure ram pivotally mounted on the tilting-lever unit. It may include an inlet ram interacting with the first tube portion and/or an outlet ram interacting with the second tube portion. At least one pressure ram can be prestressed by means of a prestressing unit, in particular by means of a compression spring, into a position opening, in particular non-contacting, the respective tube portion. In this way, it can be ensured that the pressure rams are not located in the area of the corresponding tube portion when the pump is not in operation. This allows particularly user-friendly changing, insertion and removal of the pump module according to the invention.

Since the drive/drives of the pump can be small, it is advantageously possible that the pump comprises a power storage unit, in particular a rechargeable battery, and can be operated without a direct power supply. The power storage unit can, for example, be a standard lithium battery that can be charged via a standardized connector, for example in the form of a USB interface. This can also be used to read data into and/or out of a pump controller.

In summary, it can be said that the invention allows an infusion pump system with the accuracy of a syringe pump and the delivery volume or volume reservoir of a flexible tube pump with significantly lower power requirements, reduced size, and low manufacturing costs. In particular, it provides a pump module for a piston pump, which has a stroke-controlled piston system. The pump module/pump element itself is absolutely sterile in a particularly advantageous way in the area where the infusion fluid is located. The following advantages can in particular be achieved through this invention:

- "One fits all": a wide range of (almost all known) infusion therapies can be performed with a single pump.
- Cost-effective and small infusion pump.
- The pump can be used in any place (everywhere), in particular without power supply (mobile, long battery life), which makes it particularly suitable for outdoor use or use in less developed areas.
- The pump allows more accurate dosing of the infusion than standard infusion pumps.
- Firm connection of the pump module, particularly designed as a single-use article, to the pump.
- The pump module can be coupled with different types of infusion lines.
- Both the pump module and the infusion pump are very easy to use and user-friendly.
- The system allows low as well as high feed rates both with accurate dosing.
- The system is absolutely sterile.

The drive for the piston-cylinder unit can be equipped with a rotation monitor that is not shown. This makes it possible to detect disturbances in the supply of fluid to a patient, for example an obstruction in the outlet. Such disturbances can be detected by deviations of the drive behavior from usual values, for example by blocking or slowing down the motor. By means of such rotation monitoring, the use of otherwise necessary, expensive pressure sensors can be dispensed with.

BRIEF DESCRIPTION OF THE DRAWING FIGURES

Further features and advantages of the present invention can be derived from the following exemplary and non-restrictive description of the invention by means of figures. These are only schematic in nature and serve only to understand the invention. They show:

DETAILED DESCRIPTION

Figure 1:
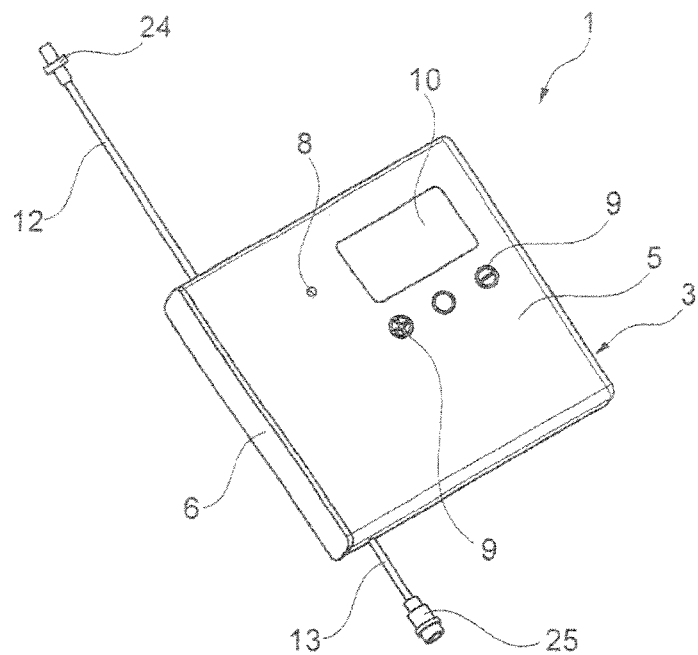
FIG. 1 shows a perspective view of an infusion pump according to the invention with inserted pump module.

FIG. 1 shows an embodiment example of an infusion pump 1 according to the invention with inserted pump module 2. The pump 1 has a housing 3, which preferably essentially consists of a lower housing part 4 with a housing lid 5 and a cover flap 6. The lower housing part 4 and the housing lid 5 are connectable to each other, for example via a latching connection or screws not shown in the figures, and form the housing 3 when assembled. The lower housing part 4 has a housing bottom 7. In or on the housing lid 5, the units/elements of pump 1 described below are arranged:
- display elements 8,
- operating elements 9 and a
- display 10.

Figure 3:
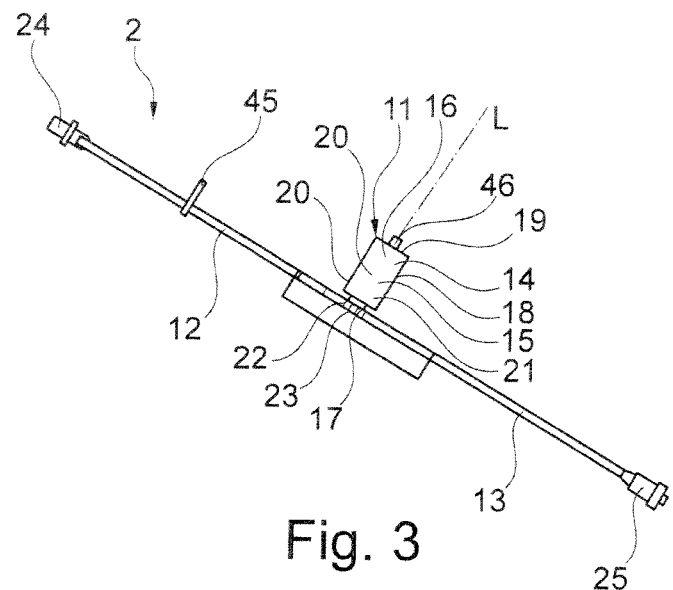
FIG. 3 shows a perspective view of a pump module according to the invention with connected hose.
Figure 4:
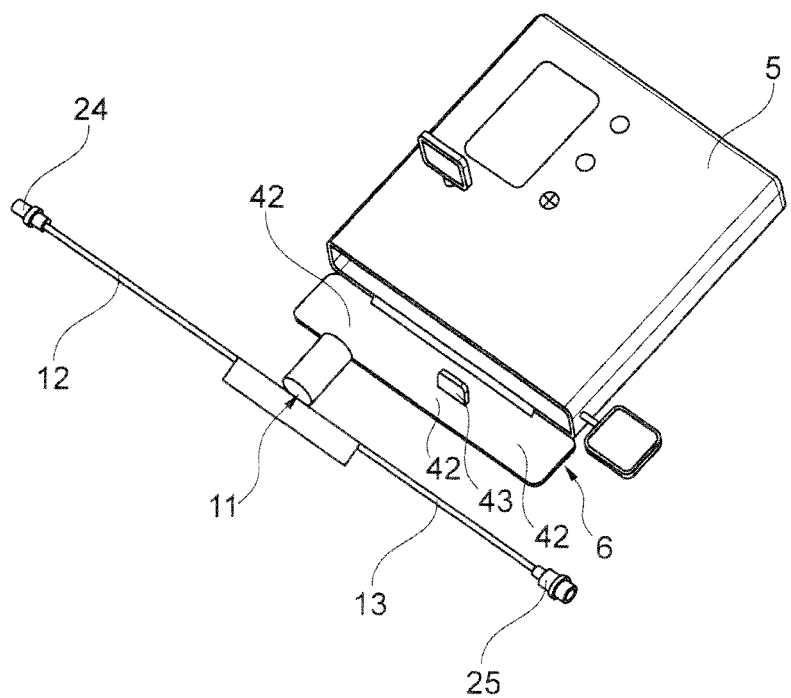
FIG. 4 shows a perspective view of an infusion pump as well as a pump module according to the invention when inserting the pump module into the pump.
Figure 6:
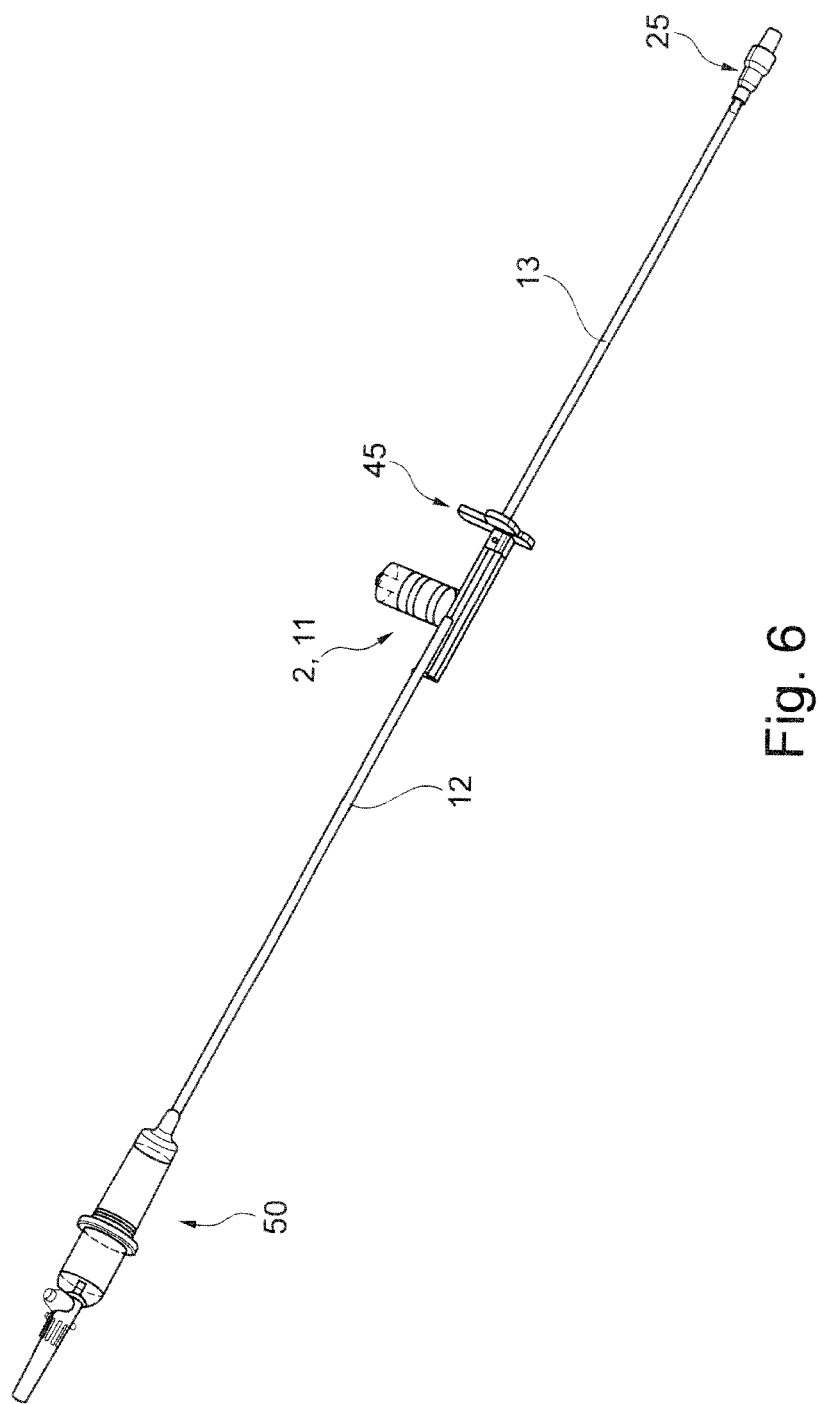
FIG. 6 shows a pump module with a drip chamber connected to it.
Figure 7:
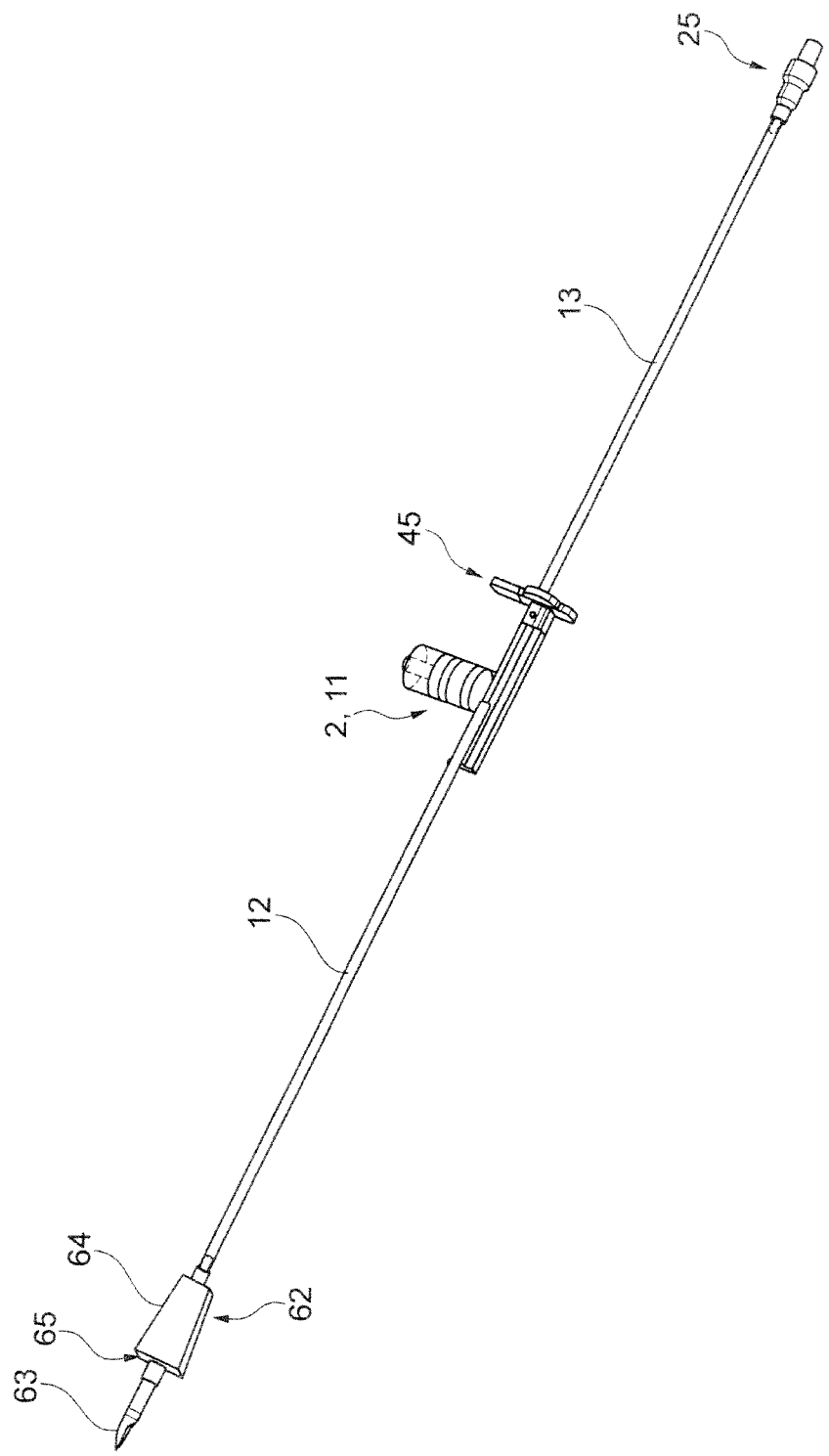
FIG. 7 shows a pump module with a spike connected to it.
Figure 8:
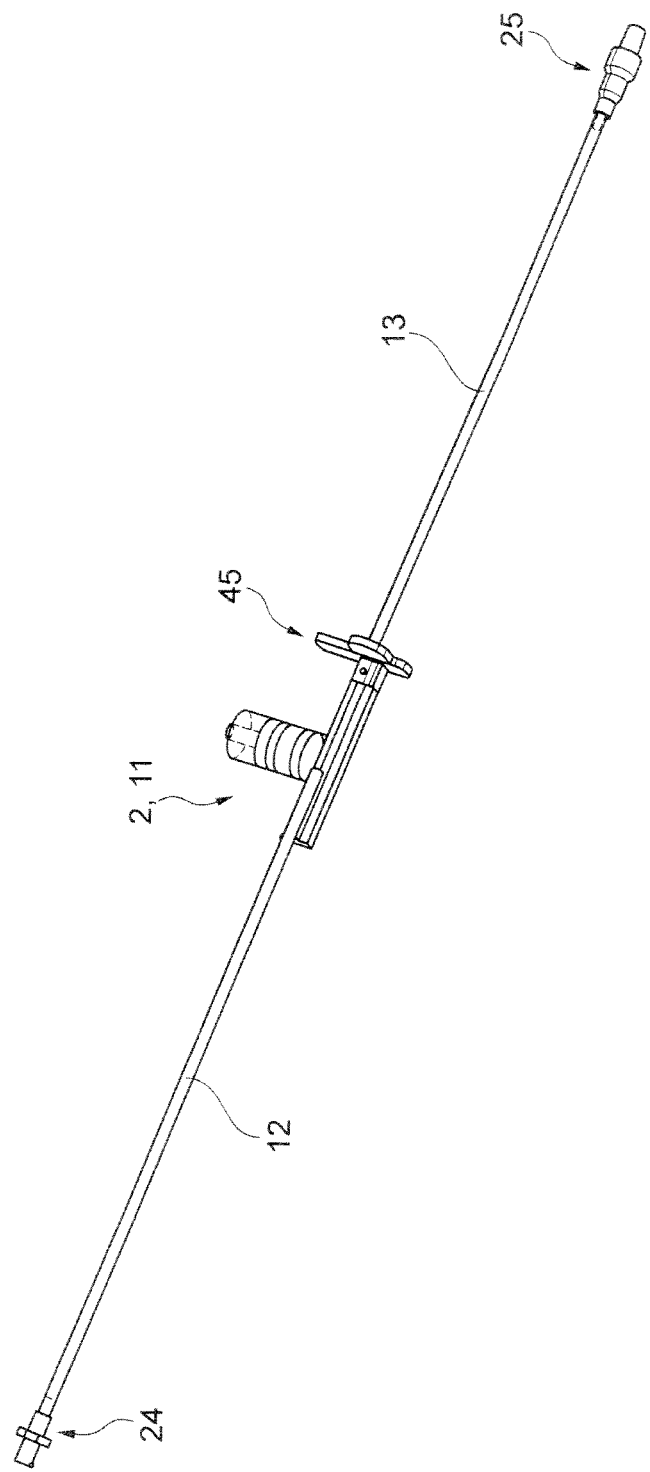
FIG. 8 shows a pump module with a Luer-Lock internal cone connected to it.

The pump module 2 is shown individually schematically in FIG. 3. A more detailed embodiment of the pump module 2 can be found in FIG. 5. FIGS. 6 to 8 also show the pump module 2. It has a piston-cylinder unit 11, a first elastically deformable tube portion 12 and a second elastically deformable tube portion 13. The pump module 2 is designed as a single-use article (single-use article, disposable article). The tube portions 12, 13 can in particular be designed as PVC tubing.

The piston-cylinder unit 11 has a cylinder 14, which may in particular consist of plastic and/or which may be made as an injection molded part, and a piston 15, which is reciprocally movable therein and which may also in particular consist of plastic and/or may be made as an injection molded part. The piston 15 is arranged on/at a piston rod 16 and fixed in position at least in the axial direction. The cylinder 14 has a bottom wall 17, a circumferential wall 18 and a lid wall 19. The piston rod 16 protrudes through an opening formed in the lid wall 19 in the axial direction L out of the cylinder 14. The piston 15 is preferably sealed with respect to the circumferential wall 18 by seals 20 arranged on both sides, so that the piston-cylinder unit 11 has a fluid space/dosing space 21. In the bottom wall 17, an inlet bore 22 and an outlet bore 23 are formed. The fluid space 21 is fluidically connected to the first tube portion 12 via the inlet bore 22 and to the second tube portion 13 via the outlet bore 23. The tube portions 12, 13 can in particular be molded on the cylinder 14. In particular, they can be formed like usual infusion tubes. In the embodiment of FIG. 3, the first tube portion 12 is provided with an inlet Luer-Lock connection 24 at its end facing away from the piston-cylinder unit 11, the inlet Luer-Lock connection 24 being formed in the present case, as in FIG. 8, as a Luer-Lock internal cone. In the embodiment of FIG. 3 as well as in the embodiments of FIGS. 6 to 9, the second tube portion 13 is provided with an outlet Luer-Lock connection 25 at its end facing away from the piston-cylinder unit 11, the Luer-Lock connection 25 being forming in the present case as a Luer-Lock outside cone. Thus, the pump module 2 can be easily connected to common infusion units.

Figure 2:
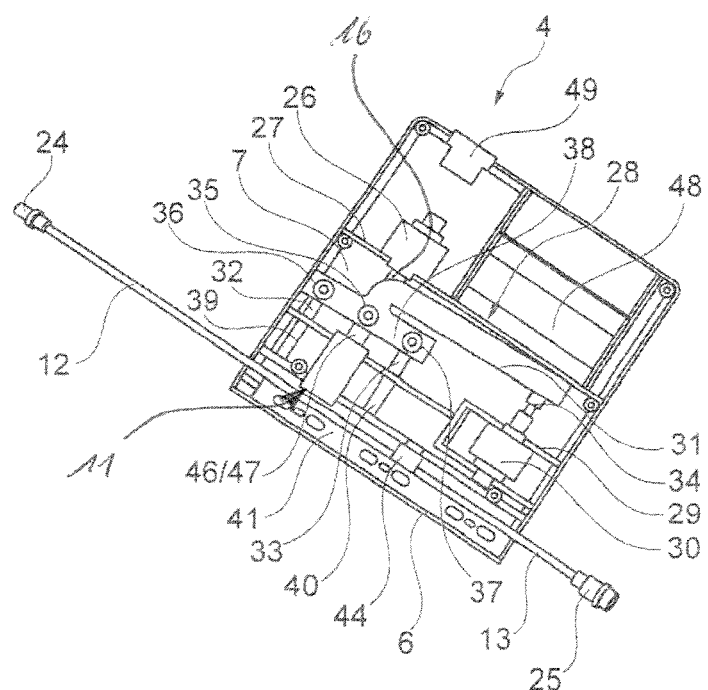
FIG. 2 shows a perspective view of an infusion pump according to the invention with inserted pump module with partially free-cut pump housing.
Figure 5:
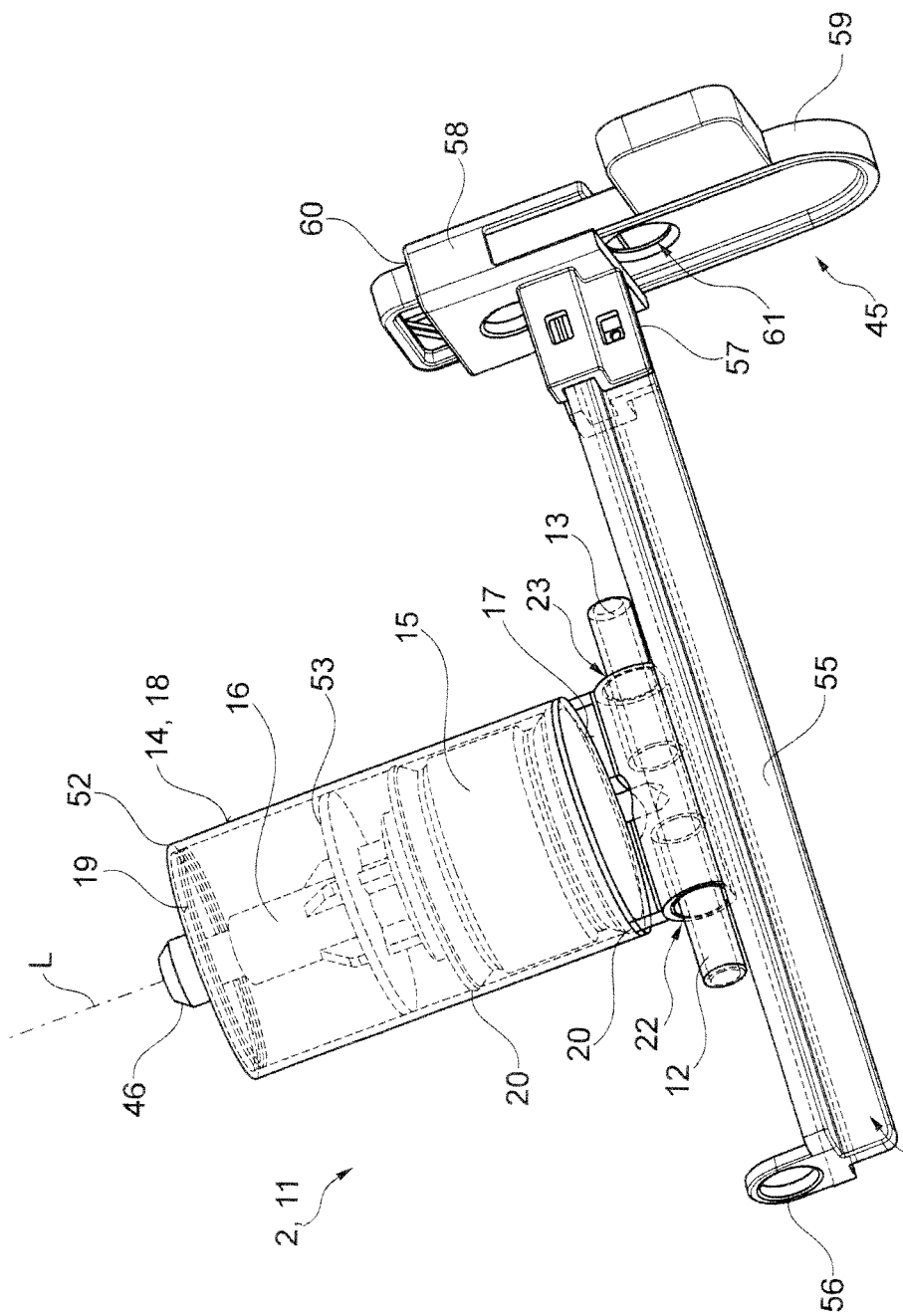
FIG. 5 shows a detailed view of a pump module with integrated sliding clamp.

FIGS. 2 and 5 show that the pump 1 has a drive 26 (in the pump) for the piston-cylinder unit 11, here in the form of a linear motor 26. The motor 26 is congruent to the longitudinal axis L of the piston rod 16 (of the piston-cylinder unit 11), so that forces for reciprocal driving of the piston 15 can be transmitted centrally and without twisting/transverse forces. The drive 26 is mounted in an intermediate wall 27 fixed in position to the lower housing part 4. The piston rod 16 can be connected to the drive 26 by means of a coupling element 46 arranged or formed on it and by a counter element 47 formed to engage with it. The coupling element 47 therefore serves as a receptacle for the drive/linear motor 26.

FIG. 2 furthermore shows that the pump 1 has a control unit 28 (in the pump) at least for controllably squeezing the tube portions 12, 13 together. The control unit 28 can be operatively connected to the first tube portion 12 and the second tube portion 13 and is arranged on the lower housing part 4 via a further intermediate wall 29. It has a motor-driven tilting-lever unit driven by means of a (driven/regulated) drive 30, here a linear motor 30, with a tilting lever 31 and two pressure rams 32, 33 (valve devices) pivotably arranged thereon. The tilting lever 31 is connected to the linear motor 30 via a carrier 34 and mounted on a titling bearing 35 so that it can pivot around the tilting axis orthogonal to the drawing plane in FIG. 2 and not shown in the figure. The pressure rams 32, 33 are pivotally mounted on a lateral arm 38 of tilting levers 31 by means of pivot bearings 36, 37 and guided on the lower housing part 4 to be linearly positionable. They are prestressed by pressure springs 39, 40 in such a way that the tension of the pressure springs 39, 40 forces them away from the two tube portions 12, 13.

FIG. 2 shows that the pressure rams 32, 33 are arranged orthogonally to the tube portions 12, 13. They are furthermore linearly positionable in a direction orthogonal to the tube portions 12, 13. The pressure rams 32, 33 are formed and arranged in such a way and are provided to squeeze the first tube portion 12 together and to release the second tube portion 13 in a first tilting position shown in FIG. 2. In a second tilting position, which is not shown in any of the figures, the pressure ram 32 on the inlet tube side is positioned away from the first tube portion 12 from the position shown in FIG. 2, i.e. displaced quasi in the direction of the motor 26, while the pressure ram 33 on the drain tube portion side is displaced in the direction of the second tube portion and squeezes it together. In this position, the first tube portion 12 is no longer squeezed by the pressure ram 32 and its flow cross-section is released. The linear motor 30 is extended in the situation shown in FIG. 2 where the first tube portion is squeezed. In the functional position described above and not shown, in which the second tube portion 13 is squeezed, it is retracted. By reciprocally extending and retracting the motor 30, the tilting lever 31 is stimulated to a tilting movement around its bearing 35, which causes the described shift of the pressure rams 32, 33.

The FIGS. 1, 2, 4 and 9 show that the cover flap 6 is arranged on the lower housing part 4 so as to be pivotable between an opened position (FIGS. 4 and 9) and a closed position (FIGS. 1 and 2). The cover flap 6 can be locked to the housing 3 by means of a locking mechanism 41 and has latching pins 42 interacting with the mechanism 41 for this purpose. It is also provided with a positioning pin 43, which interacts with the second tube portion 13 and ensures that it is placed as intended on an air sensor 44 when the cover flap 6 is closed. The drives 26, 30 of the pump are powered by a rechargeable battery 48, which can be charged via a USB port 49.

In order to use the pump 1, an operator first opens the cover flap 6 of the pump 1, for example by inserting a special key laterally into a hole provided for this purpose and unlocking the flap 6 with it. An infusion device, for example, can be connected to the Luer-Lock connection 24 of the pump module 2 from FIGS. 1 to 4 as well as 8. Furthermore, the pump module 2 is equipped with a drip chamber 50 (FIG. 6) or with an injection spike 63 (FIGS. 7 and 9), which can also be components of infusion lines designed as disposables. After the infusion line including the two tube portions 12, 13 has been filled up to the outlet Luer-Lock connection 25/the drip chamber 50/the injection spike 63 free of air bubbles, the first tube portion 12 (FIG. 3) or the second tube portion 13 (FIGS. 5 to 9) is closed in a fluidtight manner using a sliding clamp 45. Then, the operator pushes the pump module 2 into the designated receptacle of the pump 1 until the coupling element 46 of the piston rod 16 audibly and/or perceptibly engages with the counter element 47 of the drive 26 and the piston-cylinder unit 11 is connected to the drive 26. The cover flap 6 is subsequently closed. The locking mechanism 41 located in the upper housing part 5 ensures secure locking of the flap 6. At the same time, the second tube portion 13 is placed as intended in relation to the air sensor, for example it is pressed against it. This ensures that any air bubbles present or introduced during an infusion are detected and communicated accordingly.

Now, the operator enters the desired feed rate via the display elements 8 and the operating elements 9. They are displayed via display 10, which can be designed as a touch screen according to one embodiment, so that an input can also be made via the display 10 (operation via an app in the mobile phone or tablet is also possible and lies within the scope of the invention). Directly after clearance, the pump 1 starts. The linear motor 30 retracts from the position shown in FIG. 2 and the outlet ram 33 clamps the second tube portion 13 in a fluid-tight manner. At the same time, the inlet ram 32 opens the first tube portion 12. Then, the linear motor 26 for the piston 15 moves backwards from the position shown in FIG. 2 and sucks infusion solution through the first tube portion 12 into the fluid chamber 21 of the piston-cylinder unit 11. As soon as the set dosage is reached, the linear motor 30 returns to the forward position shown in FIG. 2 and the inlet ram 32 closes the first tube portion 12 in a fluidtight manner. At the same time, the outlet ram 33 opens the second tube portion 13. The linear motor 26 then moves forward to the position shown in FIG. 2 up to the stop and pushes the infusion fluid present in the fluid chamber 21 into the second tube portion 13. This process continues until the specified dosage is reached. When the infusion is finished, the cover flap 6 is opened again with the special key.

The special key can also be used to unlock the coupling between drive 26 and piston rod 16. Now, the pump module 2 can be removed from the housing 3 of the pump 1.

The detailed construction of the pump module can be seen in FIG. 5.

An annular bead 52 located in the area of the lid wall 19 (or formed on it) represents an axial stop for a limiting plate 53 preferably designed integrally with the piston rod 16. Thus, the maximum stroke of the piston-cylinder unit 11 is determined by the limiting plate 53 and a falling out of the piston 15 from the cylinder 14 is prevented by form-fit. At the end side of the piston rod 16 facing the bottom wall 17 of the cylinder 14, the piston 15 is preferably arranged/formed/fixed as a smooth-running piston. The piston is further preferably designed as a piston sleeve with a specific sleeve length or as a double piston with two axially spaced piston plates (not shown further). At its distal end and at its proximal end (or respectively distal and proximal piston plates) it has a seal 20 designed as a movable sealing lip. FIG. 5 shows that those seals 20 in a preferred embodiment example are continuously designed as ring seals in the circumferential direction, whereby a low and high pressure movement is ensured. The distance along the longitudinal direction L between the distal and the proximal seal 20 of the piston 15 exceeds the piston stroke of the piston cylinder unit 11 in the embodiment example shown. This guarantees that the cylinder wall of the fluid space/dosing space 21 is only in contact with the one distal seal 20, thus ensuring its sterility. Preferably, the excess between the distance along the longitudinal direction L between the distal and proximal seal 20 of the piston 15 and the piston stroke is at least 2 mm.

The pump module 2 also has a handle plate 54. It has a T-shape in its cross-sectional profile, which results in a kind of handle strip or handle region 55, by means of which the pump module 2 is easily graspable and can be inserted into or removed from housing 3. In concrete terms, the handle strip 55 is arranged at the distal end of the piston cylinder unit 11 in such a way that the handle strip 55 extends transversely to the cylinder longitudinal axis L, preferably perpendicular thereto, and further preferably parallel to the tube portions 12, 13. The handle strip/plate 54 is provided with a sleeve or eyelet 56 at its end facing/positioned at the first tube portion 12, which protrudes transversely to the handle strip/plate and whose longitudinal axis runs parallel to the handle strip/plate. The sleeve/eyelet 56 is preferably designed integrally with the handle strip/plate 54 and serves to fix an infusion line (e.g. the tube portion 12) which is guided through it. In this way, it defines a circular hollow section in which the infusion line lies/is inserted after its introduction. The handle strip/plate 54 is mechanically coupled to the sliding clamp 45 at its end facing/positioned at sides of the second tube portion 13. For this purpose, detention cams or flexible tongues with latching projections 57 are attached to/formed on the handle strip/plate 54, whereas an insertion chute is formed on the sliding clamp 45. The detention cams 57 are, for example, rectangular or spherical protruding elements which engage in corresponding counter eyelets/offsets/recesses in the insertion chute or its circumferential wall of the sliding clamp 45 in order to couple them to the handle strip/plate 54 in a defined position. This connection is a form closure, which is realized by snapping the counter eyelets over the detention cams 57.

The sliding clamp 45 has a rigid part or frame 58 and a movable part or slider 59 supported in the rigid part or frame 58. Both the slider 59 and the frame 58 are each formed with a through hole/opening that is congruently positioned in a first sliding position and are shifted relative to each other in a second sliding position. In the second sliding position/condition, in which the pump 1 does not deliver or the pump module 2 is not inserted in the housing 3, they clamp the first tube portion 13 in such a way that absence of air bubbles is guaranteed. In the first/further sliding position, the movable part 59 is moved relative to the rigid part 58 such that said first opening 60 formed by the rigid part 58 and the other, second opening 61 formed by the movable part 59 of the sliding clamp 45 are flush with each other (overlap), thereby releasing fluid flow through the second tube portion 13 guided through the two through holes/openings.

Figure 11:
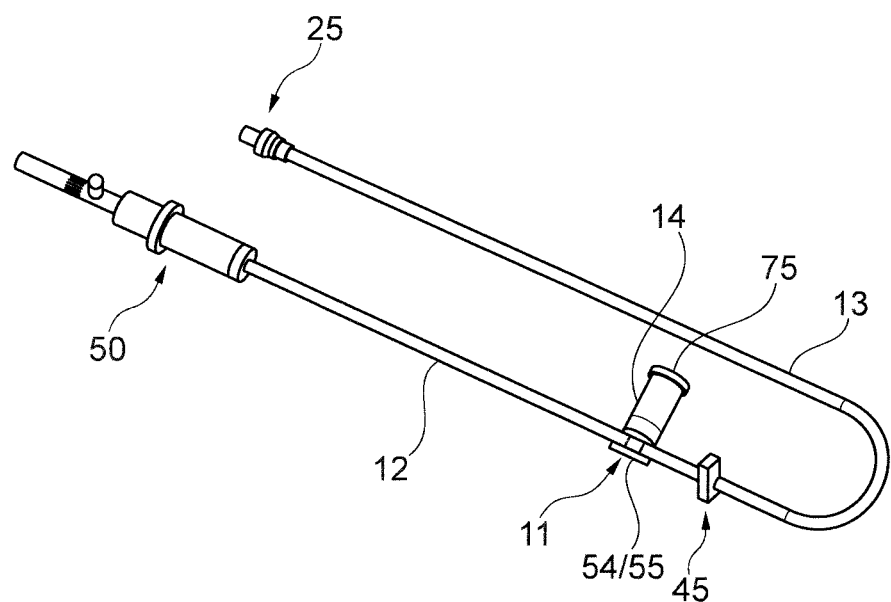
FIG. 11 shows a view of an embodiment of the pump module according to the invention.

The advantage according to the invention that the infusion pump 1 can be used for all applications of an infusion, i.e. for those with high delivery volume and those with high accuracy requirements, is further enhanced by the fact that all infusion sets can be connected to the pump. FIG. 6 illustrates as an example the coupling of the first tube portion 12 with a drip chamber 50. In this way it is possible to couple the pump module 2 with a drip chamber 50 and then to insert this unit into the housing 3. The drip chamber 50, which as a rule is part of every infusion system, can thus be arranged directly downstream of the pump module 2, which optionally increases the compactness of the entire infusion system. It serves to regulate the droplet formation of the administered liquid as well as to prevent the formation of air bubbles. FIG. 11 shows a very similar embodiment, which differs in that the sliding clamp 45 is not arranged directly on the piston-cylinder unit 11, but separately.

FIG. 7 shows a further embodiment with a different infusion set. Thus, the infusion line here shows a spike 62 downstream of the pump module 2. This spike 62 is the connecting piece that provides a reliable connection between an external infusion container and the infusion lines. The spike 62 can be divided into an injection spike 63 and a retention seat 64. Between these, a spike stop 65 is formed, which enables a safe seating of the spike 62.

Figure 9:
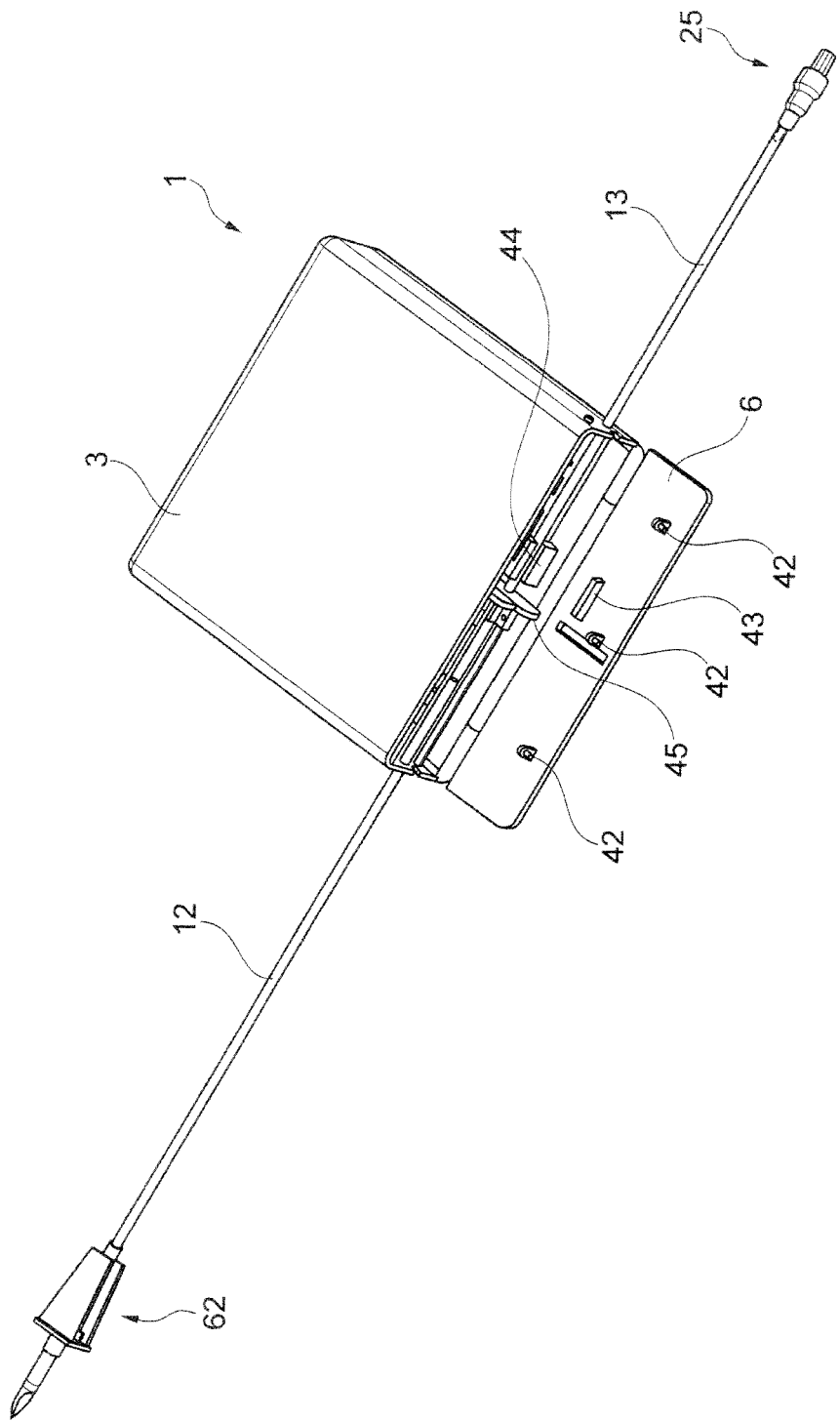
FIG. 9 shows the pump module with the spike from FIG. 7 inserted into the infusion pump according to the invention.

In FIG. 8, the first tube portion 12, as in FIG. 3, is provided with the inlet Luer-Lock connection/Luer-Lock internal cone 24. The sliding clamp 45 is in such a state that it allows a flow through the second tube portion 13. In this state, where flowing is possible, the pump module 2 is inserted into the housing 3 as shown in FIG. 2 and FIG. 9. FIG. 9 shows the embodiment in which the spike 62 is connected to the first tube portion 12.

Figure 10:
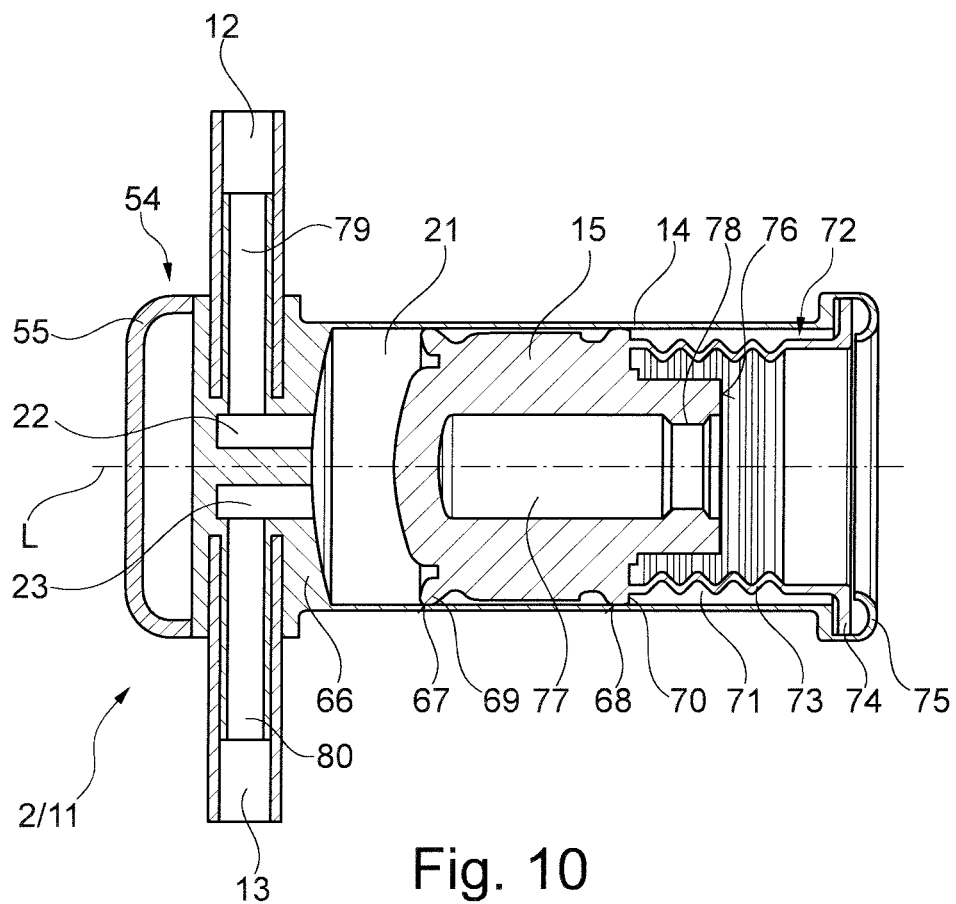
FIG. 10 shows a view of a section of the piston-cylinder unit in the axial direction.

FIG. 10 shows an embodiment of the piston-cylinder unit 11 of the pump module 2 in a view cut along the axial direction. It comprises a cylinder 14 provided at its distal end with a cylinder head 66. In this, an inlet passage 22/an inlet bore 22 and an outlet passage 23/an outlet bore 23 are formed, each of which is fluidically coupled to a connection nozzle 79, 80 for coupling the fluid feed line 12 or respectively the fluid drain line 13. The handle piece 54 with the handle portion 55 is arranged, here formed, on the cylinder head 66. This is used to handle the piston-cylinder unit 11, in particular when inserting it into the infusion pump 1.

Inside the cylinder 14, the piston 15 is arranged so that it can be moved in the axial direction L in a translatory/back and forth manner. A circumferential distal annular groove 67 and a circumferential proximal annular groove 68 are formed in the wall of the cylinder 14. These serve to receive a distal piston seal 69 or respectively a proximal piston seal 70. The piston seals 69, 70 are formed here as flexible sealing lips on the piston 15, for example using the two-component injection molding. The distance between the annular grooves 67, 68 in the direction of the longitudinal axis L (axial direction) is equal to the distance between the piston seals 69, 70 in this direction, so that the two piston seals 69, 70 can be received and supported in the corresponding annular grooves 67, 68 without great pre-tension and load by the wall of the cylinder 14 when the piston seals 69, 70 are in a resting or storage position. This ensures that they always seal well during use. Furthermore, the distance between the flexible piston seals 69, 70 in this embodiment example is about 2 mm larger than the stroke of the piston pump, i.e. than the stroke of the piston 15 in the cylinder 14. This ensures that the area coming into contact with the infusion solution is always absolutely sterile.

In the piston-cylinder unit 11, a delivery chamber 21 is formed in such a way that it is fluidically connected to the fluid feed line 12 and the fluid drain line 13, said delivery chamber 21 being delimited by the walls of the cylinder 14, the piston arranged therein, and the distal piston seal 67, which seals the piston from the cylinder. A piston displacement 71 located on the side of the piston seal 67 opposite to the delivery chamber 21 is sealed in a sterile manner against the environment by means of an elastic sealing element 72 arranged therein. The sealing element 72 is arranged on the one hand at the proximal end of the piston and on the other hand at the proximal end of the cylinder and does not protrude beyond the proximal end of cylinder 14. The sealing element 72 also has the form of a pot-shaped membrane with a bellows 73 extending essentially in the axial direction inside the cylinder 14 and a proximal annular coupling portion 74. The bellows 73 is connected in a sealing manner with its distal side facing the piston 14 on the front side of the piston 14, here connected in a material-locking manner. The ring-shaped coupling portion 74 is firmly and fluid-tightly connected to the cylinder 14 by means of a border 75 or respectively a border edge 75 on the end side. Unlike the embodiment shown in FIG. 5, the piston 15 is provided with a piston-rod accommodation 77 in the form of a central blind hole 77 at its proximal front surface 76, which is introduced in the axial direction L in the proximal front surface 76 of the piston 15 and has an internal latching structure 78, here in the form of a fixing ring 78, for the latching receiving of a piston rod 16 of the drive mechanism.

For use, an operator inserts the piston-cylinder unit 11 of the pump module 2, which is filled bubble-free with infusion solution, into the intended device of the infusion pump 1. The piston rod 16 is inserted into the piston-rod accommodation 77 of piston 15 and latches into the latching structure 78. The operator sets a certain feed rate on the infusion pump 1 and starts the system. The piston rod 16 now moves the piston 15 back and forth with a stroke of 10 mm, for example, and delivers the infusion solution towards the patient. The greater distance of the piston seals 69, 70, for example a distance of 12 mm, ensures that the area lying between them always remains sterile. The sealing element 72 also keeps the proximal area of cylinder 14 sterile.

The invention claimed is:

1. A pump module for an infusion pump, the pump module comprising:
    a piston-cylinder unit comprising an inlet bore and an outlet bore separate from the inlet bore;
    a fluid feed line connected to the inlet bore; and
    a fluid drain line connected to the outlet bore,
    the piston-cylinder unit, the fluid feed line, and the fluid drain line forming a modular unit that is insertable into and removable from an infusion pump housing,
    the piston-cylinder unit adapted for delivering fluid from the fluid feed line into the fluid drain line to a patient,
    the piston-cylinder unit comprising a delivery chamber fluidically connected to the fluid feed line and the fluid drain line and which is delimited by a cylinder, a piston arranged therein so as to be movable in a forwards/backwards movement in an axial direction, and by a piston seal which slidably seals the piston with respect to the cylinder,
    the fluid feed line and the fluid drain line each extending lengthwise in a direction transverse to the axial direction,
    the piston seal comprising a sleeve portion extending along and surrounding the piston, the sleeve portion being formed to be movable relative to the piston and being loosely held between a circumferential/wall portion of the cylinder and the piston and being sealingly fixed to an end or end region of the cylinder facing away from the delivery chamber, such that:
    a section of the peripheral circumferential/wall portion of the cylinder which is passed by the piston seal during the forwards/backwards movement of the piston is sealed in a sterile manner with respect to the environment,
    wherein the piston seal further unit comprises a proximal piston seal and a distal piston seal which both seal between the piston and the cylinder and ensure a sterility of the delivery chamber, and the cylinder is provided on an inner surface facing the piston with a circumferential annular groove for receiving the proximal piston seal or the distal piston seal in a storing position/rest position therein.

2. The pump module according to claim 1, wherein a piston displacement located on a side of the piston seal opposite the delivery chamber is sealed in a sterile manner by an elastic sealing element which is arranged therein and forms the sleeve portion, which is arranged at a proximal end of the piston and at a proximal end of the cylinder, wherein the sealing element does not project beyond the proximal end of the cylinder.

3. The pump module according to claim 2, wherein the elastic sealing element has an axial section which is designed as a bellows and which extends in the axial direction and is arranged inside the cylinder.

4. The pump module according to claim 2, wherein the elastic sealing element has, on a side facing away from the piston, an annular coupling portion for sealing arrangement on or connection to the cylinder, said annular coupling portion being sealingly connected to the cylinder by a border of the cylinder, and/or the elastic sealing element, with a side facing the piston, is sealingly connected to a front side of the piston.

5. The pump module according to claim 2, wherein the piston comprises a coupling structure for releasable coupling with a corresponding coupling element of a drive mechanism of the infusion pump.

6. The pump module according to claim 5, wherein the coupling structure is formed radially inside the elastic sealing element.

7. The pump module according to claim 5, wherein the coupling structure has a blind hole which is introduced in the axial direction into a proximal front surface of the piston.

8. The pump module according to claim 1, wherein the proximal piston seal and the distal piston seal are arranged plane-parallel to each other and/or a distance in the axial direction between the proximal piston seal and the distal piston seal is greater than a delivery stroke of the piston-cylinder unit/the piston in the cylinder.

9. The pump module according to claim 1, wherein the proximal piston seal and/or the distal piston seal is or are formed in one piece with the piston.

10. The pump module according to claim 1, wherein the cylinder has a cylinder head at a distal end of the cylinder, and wherein at least one fluid passage is formed in the cylinder head that fluidically connects the delivery chamber to the fluid feed line and to the fluid drain line.

11. The pump module according to claim 1, wherein a handle piece is arranged distally on the cylinder for handling the pump module during coupling and uncoupling with the infusion pump.

12. The pump module according to claim 1, wherein the piston-cylinder unit comprises a first connection nozzle projecting from the piston-cylinder unit in a first direction and a second connection nozzle projecting from the piston-cylinder unit in a second direction opposite the first direction, the first and second connection nozzles extending transversely to the axial direction.

13. The pump module according to claim 12, wherein the first connection nozzle is connected to the inlet bore and the second connection nozzle is connected to the outlet bore.

14. The pump module according to claim 1, wherein the fluid feed line and the fluid drain line are molded on the cylinder.

15. The pump module according to claim 1, further comprising a clamp attached to one of the fluid feed line and the fluid drain line, the clamp operable to close said one of the fluid feed line and the fluid drain line in a fluid tight manner prior to inserting the pump module into the infusion pump housing.

16. The pump module according to claim 15, wherein the clamp comprises an integrated slider clamp comprising a frame and a slider that is movable relative to the frame to close said one of the fluid feed line and the fluid drain line in a fluid tight manner.

17. An infusion pump for delivering fluid from a fluid source to a patient, the infusion pump comprising:
 a pump module according to claim 1; and
 an infusion pump housing, the pump module being insertable into and removable from the infusion pump housing.

18. The infusion pump according to claim 17, wherein the infusion pump housing comprises a tilting-lever mechanism having a first ram and a second ram, the tilting-lever mechanism being movable between a first tilting position in which the first ram closes the fluid feed line and a second tilting position in which the second ram closes the fluid drain line.

* * * * *